United States Patent [19]

Erdman et al.

[11] Patent Number: 5,330,598

[45] Date of Patent: Jul. 19, 1994

[54] METHOD OF MANUFACTURING AN ABSORBENT GARMENT WITH TARGET REGION AND END CAPS

[75] Inventors: Edward P. Erdman, Renton; Heinz Pieniak, Des Moines, both of Wash.

[73] Assignee: Paragon Trade Brands, Inc., Federal Way, Wash.

[21] Appl. No.: 929,812

[22] Filed: Aug. 14, 1992

[51] Int. Cl.$^5$ .................. A61F 13/15; B32B 31/08
[52] U.S. Cl. ................... 156/164; 156/160; 156/229; 156/265; 156/494; 604/385.2
[58] Field of Search ............ 156/163, 164, 160, 229, 156/494, 265; 604/385.2

[56] References Cited

U.S. PATENT DOCUMENTS

| | | | |
|---|---|---|---|
| 4,300,967 | 11/1981 | Sigl | 156/164 |
| 4,450,026 | 5/1984 | Pieniak et al. | 156/164 |
| 4,595,441 | 6/1986 | Holvoet et al. | |
| 4,662,877 | 5/1987 | Williams | |
| 4,704,115 | 11/1987 | Buell | |
| 4,704,116 | 11/1987 | Enloe | |
| 4,738,677 | 4/1988 | Foreman | |
| 4,753,646 | 6/1988 | Enloe | |
| 4,846,823 | 7/1989 | Enloe | |
| 4,990,147 | 2/1991 | Freeland | 604/385.2 |
| 4,992,125 | 2/1991 | Suzuki et al. | 156/164 |
| 5,034,007 | 7/1991 | Igaue et al. | |
| 5,061,261 | 10/1991 | Suzuki et al. | 604/385.2 |
| 5,110,386 | 5/1992 | Ochi et al. | |

FOREIGN PATENT DOCUMENTS 3286761 12/1991 Japan .................. 604/385.2

OTHER PUBLICATIONS

"Ultra 1992—Preliminary R&D Overview of Timing, PPD Steps, Features, Approaches and Issues," Heinz Pieniak, May 13, 1991.

Primary Examiner—Jeff H. Aftergut
Attorney, Agent, or Firm—Klarquist, Sparkman, Campbell, Leigh & Whinston

[57] ABSTRACT

An absorbent garment includes a moisture impervious outer layer, a nonwoven moisture pervious inner layer having an upper waste receiving surface, and an absorbent layer between said inner and outer layers, each of which layers extends between said front and back edges. The garment further includes a pair of overlay strips applied over the upper waste receiving surface with the opposite ends of the strips superimposed. Each overlay strip typically has one substantially straight longitudinal edge and one longitudinal edge with an inset central portion whereby the strips provide an opening to expose a target region in a central portion of the garment body. This superimposition of the strips also forms a pair of end caps for preventing fluid leakage at the garment body front edge and the garment body back edge. A stretchable material is positioned in a stretched condition along the longitudinal edges to urge the overlay strips into contact with the wearer's body.

11 Claims, 6 Drawing Sheets

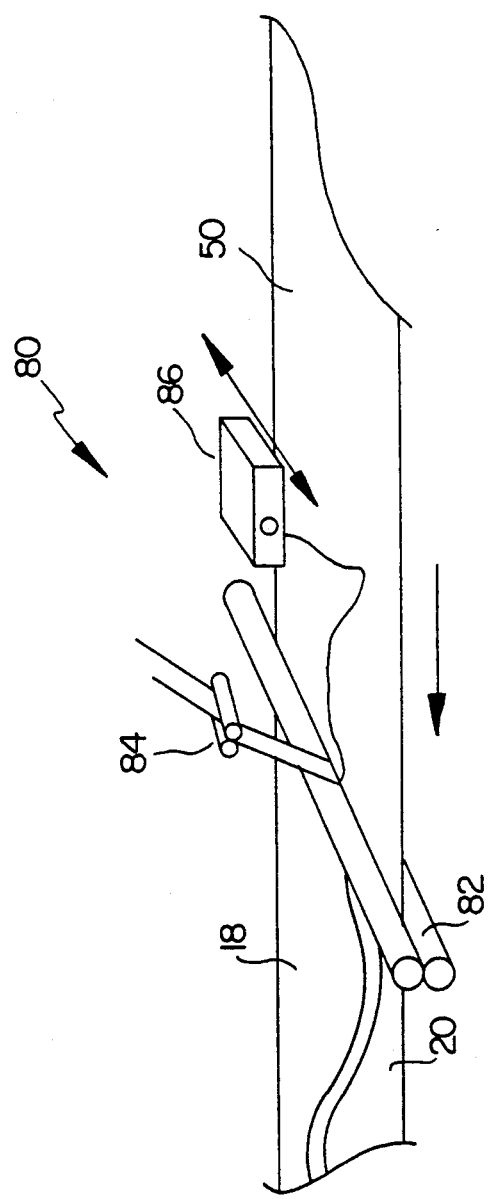

METHOD OF MANUFACTURING AN ABSORBENT GARMENT WITH TARGET REGION AND END CAPS

BACKGROUND OF THE INVENTION

The present invention relates generally to a disposable absorbent garment, such as a diaper, and more specifically to an improved garment design and method for producing the same which incorporates overlay strips which define a target region and form end caps.

The manufacture of disposable absorbent garments, such as infant diapers or adult incontinence briefs is well-known in the art. Traditionally, disposable diapers are constructed with a moisture impervious outer or backing layer, a moisture pervious body-contacting inner layer, and a moisture absorbent core layer sandwiched and encased between the inner and outer layers. More recently, elasticized waist bands and elasticized leg openings have been developed to provide a better fit and enhance the containment of bodily exudates.

Though elasticized waist bands and elasticized leg openings have enhanced containment of bodily exudates, they have not been entirely successful in preventing leakage. When a person voids, exudate is released relatively quickly at a localized region of the crotch portion of the disposable garment. This release is relatively fast and can overwhelm the garment's ability to absorb the exudate, possibly resulting in the wicking and overflow of exudate from the garment to clothing contacting the edges of the garment.

Therefore, there is a need to further enhance the containment of bodily exudates. Some disposable garments are presently being produced which include barrier cuffs, standing flaps, end shields, and target areas.

The concept of forming standing leg flaps is shown in U.S. Pat. No. 4,846,823 to Enloe which discloses diapers with elasticized side pockets. A pair of side pockets or standing flaps are made of water pervious material. The standing flaps extend the length of the garment and are elasticized to urge the standing flaps upward toward the body when the garment is worn. This configuration is described within this reference as slowing the sideways flow of fluidic material and as stopping essentially all the sideways flow of solid material. The Enloe design has several drawbacks. First, there is a lack of end caps. Although standing flaps alone are understood to assist in arresting the sideways flow of exudates, they do not contain the exudate flow towards the front and back waist edges. Also, the Enloe design requires extensive additional manufacturing to form these standing flaps.

The concept of forming end shields to prevent the flow of exudates to the waist end edges is shown in U.S. Pat. No. 4,753,646 to Enloe. Enloe teaches attaching waist flaps or end shields transversely across the front and back waist end edges of a garment. However, this design is understood to require the attachment of separate transversely extending end pieces as a separate and distinct step in the manufacture of the garment. The added step complicates the manufacturing process.

U.S. Pat. No. 4,738,677 to Foreman discloses an absorbent garment with barrier cuffs along the side edges and waist end edges of the garment. These cuffs have an elastic member along their edges which are described as performing the function of spacing the distal edges of the cuffs away from the liquid receiving surface of the garment when the garment is worn. This approach is also complicated from a manufacturing perspective because of the use of separate pieces for the side cuffs and waist cuffs of the garment.

The concept of forming a target area in an absorbent garment is shown in U.S. Pat. No. 4,662,877 to Williams which discloses a shaped disposable diaper which has a target area opening formed in a hydrophobic facing sheet. The facing sheet is attached to the upper surface of the garment such that it is in primary contact with the body. The facing sheet contains a substantially oval target opening central to the garment, creating an area or target through which exudate flows to a fibrous absorbent batt or core. The facing sheet contains zones of elastication along only the side margins of the oval opening to apply tensioning forces to the facing sheet and to urge this sheet away from the batt structure at the region adjacent the opening. To practice the Williams patent, the oval opening from the facing sheet is understood to be cut and then discarded or processed as scrap material. Therefore, the manufacturing process is wasteful. Also, Williams provides zones of elastication located only on two opposing sides of the opening. Consequently, areas of the facing sheet at the ends of the opening tend to remain flat against the absorbent core where they do not as readily capture exudate migrating toward the waist end edges of the garment.

In U.S. Pat. No. 4,595,441 to Holvoet et al, a strip of liquid impermeable foil is cut in a trapezoidal wave pattern (FIG. 2 or 14) to form two strips. These strips are then shifted longitudinally relative to one another and incorporated into a garment with the deeper cuts in each strip adjacent to one another forming a target at a central area of a diaper and with the shallower cuts of each strip overlapping. A nonwoven material top sheet is then positioned over the top of the foil to complete the garment. The Holvoet et al approach is understood to lack a structure for containing exudates. When a person voids in such a diaper, the excess exudate which cannot be absorbed quickly enough by the absorbent batt will tend to flow over the nonwoven top sheet surface of the garment and outwardly from its edges.

Therefore, a need exists for an improved disposable absorbent garment design, suitable for use on adults, babies or persons of ages therebetween, which can be manufactured efficiently and which is not susceptible to the above and other limitations and disadvantages.

SUMMARY OF THE INVENTION

It is an overall object of the present invention to provide an improved disposable absorbent garment design.

It is a further object of the present invention to provide a disposable absorbent garment which is economical to manufacture.

An additional object of the present invention is to provide a disposable absorbent garment which minimizes leakage of exudates at the leg and waist edges, and which thereby minimizes the escape of moisture and solids to the outer garments of a wearer.

It is a further object of the present invention to provide an absorbent garment design which provides effective containment of exudates while overcoming certain manufacturing complexities commonly found in producing prior art garments with barrier cuffs or standing gathers or flaps and end shields.

It is also an object to provide a disposable absorbent garment designed to be constructed inexpensively and efficiently in a high speed disposable diaper or other garment manufacturing machine, while at the same time providing exceptional performance in containing and absorbing exudates.

According to one aspect of the present invention, a disposable absorbent garment is provided including a moisture impervious outer layer or backing sheet, a nonwoven moisture pervious inner layer or top sheet, and an absorbent layer sandwiched between the inner and outer layers. The garment has opposed front and back waist end edges and two opposed side margins. A pair of overlay strips of nonwoven material are attached over the top of the inner layer. Each overlay strip has first and second longitudinal edges. The first longitudinal edge has an inset portion positioned so as to form a strip that is wide at the opposite ends of the garment and narrower at the garment center. The overlay strips are superimposed to form a boundary about a target region in a central portion of the garment. This superimposition of the overlay strips forms a pair of end caps for minimizing exudate leakage at the garment body waist end edges. A stretchable material is attached or formed along the first longitudinal edges of the overlay strips and operates to urge the overlay strips into contact with the wearer's body. The stretchable material preferably bounds the entire perimeter of the target region, thus tending to lift the portions of the strips bounding the entire target region opening into contact with the wearer's crotch. When the wearer of the garment voids, the exudate is directed to the moisture pervious nonwoven inner layer and underneath the overlay strips where the exudate can be absorbed by the core. This minimizes leakage of the exudates both at the waist end edges and side edges of the garment.

In addition, this overlay sheet structure may be manufactured in an efficient manner utilizing a strip of overlay material while minimizing the generation of scrap material during manufacture of overlay strips. In the preferred manufacturing approach, the overlay strips are severed from a single piece of overlay material, preferably on a continuous basis from roll stock of this material as the material is unrolled. A serpentine path or repeating concave convex cut line is provided having a repetition pattern which alternately approaches one side edge and then the other of the overlay sheet material. The pitch of this pattern is preferably equal to the garment length. Following severing, the resulting strips are offset longitudinally by one-half of the pattern pitch and adhered to the top surface of the garment. These strips are positioned on the top surface of the garment so that the end portions of these strips are overlapping at the waist end edges of the garment and the strips bound an opening at a central portion of the garment, that is spaced from the waist end edges, the opening communicating with underlaying absorbent material of the diaper. Most preferably the severed portions of each strip are tensioned and are of a stretchable material such that the overlay strips tend to raise away from the absorbent top surface of the garment when the garment is worn. Elastic members may be positioned and secured along the edges of the strips before severing.

These and other objects, features and advantages of the present invention will become apparent to those skilled in the art from the following description and drawings. The present invention relates to the novel objects, advantages and features thereof individually as well as collectively.

BRIEF DESCRIPTION OF THE DRAWINGS

FIG. 9 is a perspective view of one form of an apparatus used in the production of the overlay strips for the garment of FIG. 1.

DETAILED DESCRIPTION OF PREFERRED EMBODIMENTS

Figure 1:
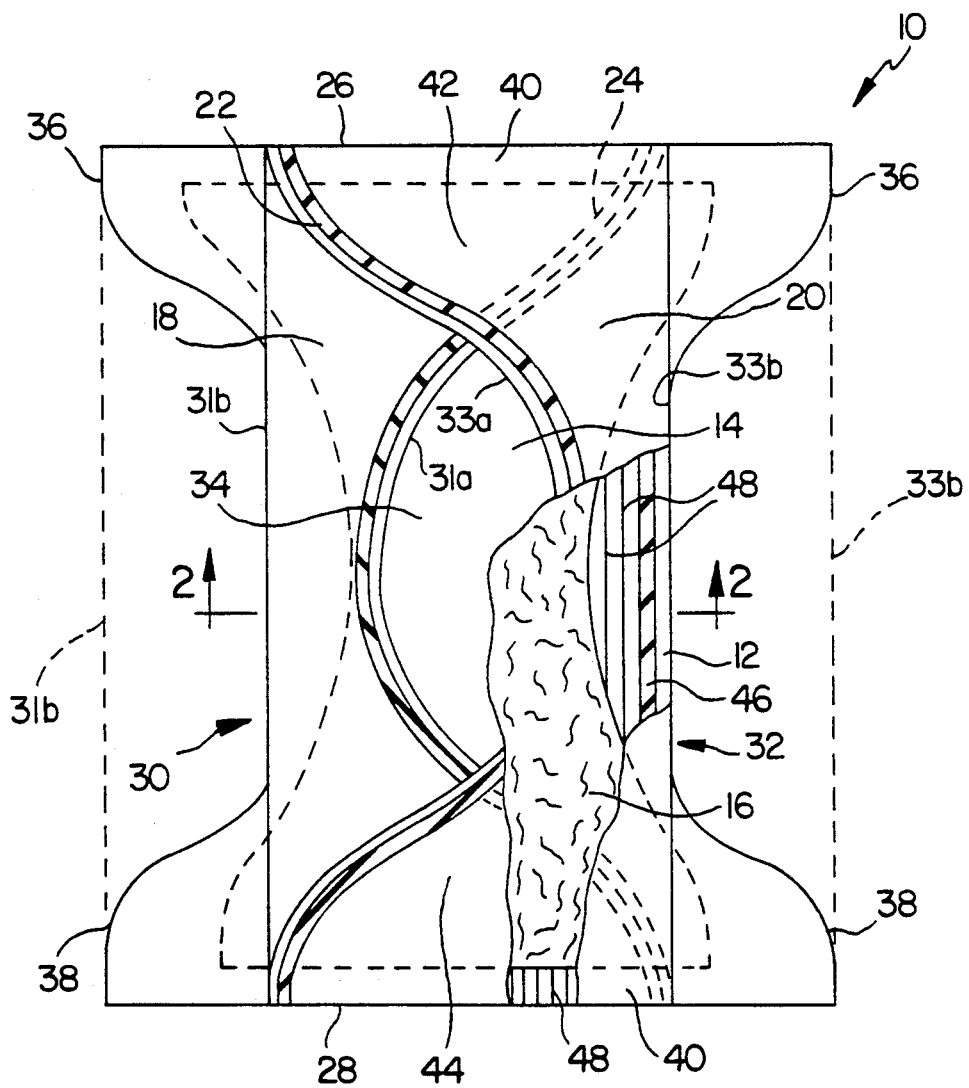
FIG. 1 is a partially broken away top plan view of one form of a disposable absorbent garment of the present invention.

FIG. 1 illustrates an embodiment of a disposable absorbent garment 10 manufactured in accordance with the invention having a moisture impervious outer or backing layer 12 and a moisture pervious inner layer 14, typically of a nonwoven material. A moisture absorbent layer or core 16 is sandwiched and encased between the inner layer 14 and the outer layer 12. The encasement of the garment may be accomplished by adhesively or otherwise bonding the layers together in a conventional manner. The core 16 is typically of wood pulp or other absorbent fibers with or without superabsorbent particles. The core may also be of a multilayer construction. These garments also typically include outer leg gathers or seals, stretchable waist bands, and tapes or other fasteners at the waist.

The disposable absorbent garment 10 is typically used as a baby or infant diaper or as an adult incontinence brief. The manufacture of such a garment is well-known in the art. One garment and method of manufacture is illustrated in U.S. Pat. No. 4,726,807, which is incorporated by reference herein. Another example is set forth in U.S. Pat. No. 4,738,677 which is also incorporated herein by reference.

Due to wide variety of core, top sheet and backing sheet constructions and materials, the invention is not limited to any specific materials or constructions of these components.

As a specifically exemplary preferred material for the backing sheet, the moisture impervious outer layer 12 may be of a thin thermoplastic material, such as a pigmented polyethylene film having a thickness in the range of 0.02–0.04 mm. The moisture permeable inner sheet 14 may, as a specifically preferred example, be of a carded polyester fiber with a latex binder or of a spunbonded polypropylene having continuous fibers and thermally bonded by patterned calendar rolls. The moisture absorbent core 16, as a specifically preferred example, may be of wood fibers or other fibers such as chemical wood pulp, or any other suitable liquid absorbing material such as commercially available fluff pulp or of a fluffed bleached kraft softwood pulp. Again, the recitation of these exemplary preferred materials are not to be construed as limiting the scope of the present invention.

The garment 10 also has a front waist end edge 26, which may lie along the front waist of a wearer, and an opposed back waist end edge 28, which may lie along the waist at the wearer's back. Two opposed garment side margins or edges 30 and 32 define leg enclosing openings when the garment is fitted on a wearer. Thus, with the front waist edge 26 positioned to the front of a wearer, side margin 30 is the left leg side margin and side margin 32 is the right leg side margin.

As shown in the embodiment of FIG. 1, the backing sheet layer 12 may extend outwardly from each of the opposed side margins 30, 32 along the front and back waist end edges 26, 28. In this manner, a pair of front waist extensions 36 are formed, extending from each side margin along the front waist edge 26. A pair of back waist extensions 38 are formed extending from each side margin along the back waist edge 28. The core layer 16 may assume an hourglass shape and extend partially over the waist extensions 36, 38 or it may simply be rectangular or of some other configuration. The inner layer 14 may be coextensive with the backing sheet layer 12 or may terminate just beyond the outer boundary of the absorbent core 16 along an outer boundary 40. The outer boundary 40 defines the region at which the inner sheet 14 is bonded or joined to the outer sheet 12 to encase the absorbent core 16.

Thus, the garment 10, as illustrated in FIG. 1, typically has an overall hourglass shape. The top and bottom of the hourglass shape form the respective front and back waist end portions of the garment. The crotch portion of the garment is central to the hourglass shape, and has a narrower width than the waist portions.

This invention features a new and improved disposable absorbent garment design for targeting exudates to an inner waste receiving surface of the inner layer 14 where moisture can be absorbed into the core 16. As shown in FIG. 1, a pair of overlay strips 18, 20 are attached over the top of the inner layer 14. The overlay strips may be of any suitable material, but are preferably soft due to their contact with the skin of a user of the garment. More specifically, the overlay strips may be of the same types of material as the facing layer 14. However, most preferably the overlay material is a nonwoven hydrophobic material so as to be both soft and capable of directing exudates toward the liquid pervious face sheet layer 14. A specifically preferred overlay strip material is a spunbonded polypropylene material, basis weight 0.6 ounces per square yard, and sold under the brand name Berkeley III by Kimberly Clark Corporation. Overlay strip 18 has respective inner and outer longitudinal edges 31a, 31b while overlay strip 20 has respective inner and outer and longitudinal edges 33a, 33b. The edges 31b and 33b are preferably straight so that the strips may be readily cut from roll stock or sheet stock (see FIG. 4) with the factory edges of the stock being the edges 31b and 33b. The edges 31a, 33a are shaped to provide an inset portion at a central region of the garment, the inset being a portion where these edges diverge from and then reconverge toward one another to define a target opening 34 therebetween which communicates with the facing sheet layer 14. The edges 31a, 33a in the most preferred embodiment follow a repeating concavo convex and most preferably a sinusoidal path with each edge tracing 180° along the path and the respective strips being offset longitudinally 90° along the path to define the target opening 34. The illustrated opening is ovoid in shape with curved longitudinal side boundaries to minimize sharp edges which could irritate a wearer of the garment. The edges 31a, 33a may be of other shapes as well, such as with rectangular or trapezoidal inset portions which still provides the desired target. Preferably the target is about one-half the garment length in width and about three-fourths the width of the garment at the width of layer 16 at the crotch, although this may be varied. A specific example is a target which is at least about eight to nine inches long and about three inches wide, although its dimensions and position may be varied. In the illustrated embodiment, the longitudinal edges with the inset central portion have a substantially sinusoidal shape.

The overlay strips 18, 20 are superimposed to define the target opening in a central portion of the garment 10 between and spaced from the opposing side edges 30, 32. The target opening is bounded by the inset central portions of the edges 31a, 33a of the overlay strips 18, 20. This superimposition of the overlay strips 18, 20 also forms a pair of end caps 42, 44 at the waist end portions of the garment for minimizing fluid leakage at the garment body front edge 26 and the garment body back edge 28. The front end cap 42 is formed between the target opening 34 and the front waist edge 26. The back end cap 44 is formed between target opening 34 and the back waist edge 28. Although variable, most preferably the strips 18, 20 overlay the outermost 25% of the diaper core 16 at the waist ends of the garment to provide an enhanced exudate barrier at these end locations.

In FIG. 1, the outer longitudinal edges 31b, 33b are straight and are spaced apart a distance which is equal to the width of backing sheet 12 at the crotch of the garment. The strips 18, 20 are typically bonded to the garment top sheet 14 adjacent to the outer edges 31b, 33b such as by one or more longitudinally extended beads of adhesive extending the full length of the garment. Consequently, the bonding, being spaced from edges 31a, 33a allows these latter edges to lift up away from sheet 14 when the garment is worn, as explained below. As shown in dashed lines in FIG. 1, the overlay strips may be wide enough so that the strips 18, 20 overlay the entire width of the garment, including extensions 36, 38. In this case, during manufacturing of the garment the edges 31b, 33b would be cut to follow the desired hour glass shape of the outer garment side edges.

Figure 3:
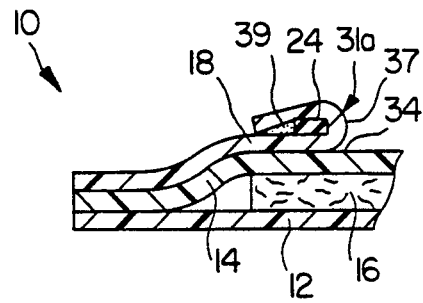
FIG. 3 is a vertical sectional view of a garment with overlay strips of the present invention wherein the overlay strip material encapsulates an elastic member so that the overlay strip material and not the elastic member is exposed to the wearer of the garment.
Figure 4:
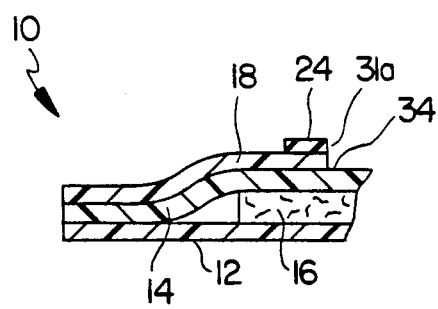
FIG. 4 is a vertical sectional view of a portion of the garment of FIG. 2 with the elastic member 24 coextensive with the edge of the overlay strip 18.
Figure 5:
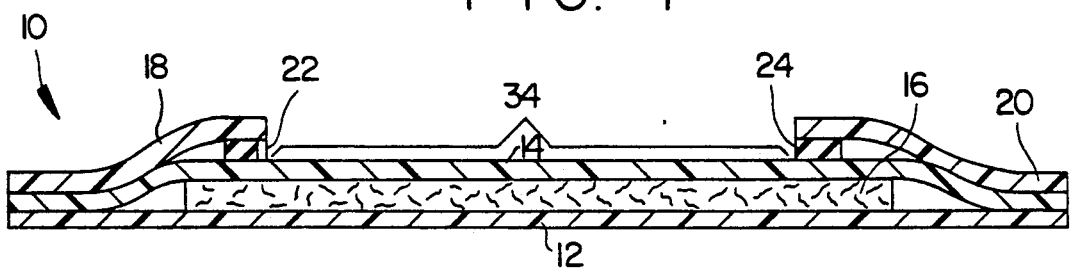
FIG. 5 is a vertical sectional view like that of FIG. 2 of an alternative embodiment of the invention.

Also illustrated in FIG. 1, the overlay strips have stretchable material along their inner edges 31a, 33a. In the illustrated embodiment, a pair of elastic members or strips 22, 24 are bonded in a stretched or tensioned condition along the entire length of each of the edges 31a, 33a. As used herein, the term "bonded" refers to adhesive bonding, sonic bonding, heat bonding, solvent bonding, stitching or any other method of affixation known or hereafter discovered. These elastic members urge the overlay strips 18, 20 into contact with the wearer's body. FIGS. 1, 3 and 4 illustrate embodiments of the invention in which the elastic member 22, 24 are bonded to the body contacting side of the overlay strips 18, 20. FIG. 5 illustrates an embodiment wherein the elastic members 22, 24 are bonded to the underside of each overlay strip relative to the body contacting surface thereof. These elastic members may further be overlayed by fabric or enclosed within a loop of the overlay strip formed by folding the edges 31a, 33a over the elastic and fastening the folded material in place, one such loop being shown as 37 in FIG. 3. In this case, the looped portion 37 of the overlay strip, and not the elastic member (e.g. 24) is in contact with the wearer, adding to the comfort of the garment. The loop is typically bonded to the overlay strip, such as by a longitudinally extending adhesive bead, a portion of which is indicated at 39. The elastic members may comprise stretchable fabric, a preferred example being BMF 89958-45-1133C from 3M Company which is stretched 100% of its length, fastened to the edges 31a, 33b of the strips 18, 20 (e.g. by hot melt adhesive) and with the tension being released when the garment is complete. Other elastic members may also be used, such as a material fastened to edges 31a, 33a and rendered elastic by the application of heat or otherwise, a specific example of a heat activated material being thermally activated elastic (TAE) from 3M Company.

In accordance with the invention, the design of the absorbent garment 10 thus defines the target region 34 bounded by the overlay strips 18, 20. The pair of elastic members 22, 24 which are bonded in a stretched condition to their respective overlay strips surround the entire target opening 34. This configuration lifts the strips surrounding the entire target region opening to make contact with the wearer's crotch. Therefore, when the wearer voids, the exudate goes directly to the moisture pervious nonwoven inner layer 14 and underneath the overlay strips 18, 20 where the exudate can be absorbed by the core 16. This design minimizes the risk of exudate leaking at the legs and waist edges of the garment by forming a standing gather around the entire periphery of the target opening 34. This design therefore proves the advantages of both standing gathers and end caps without requiring separate end caps and side leg gathers.

Figure 6:
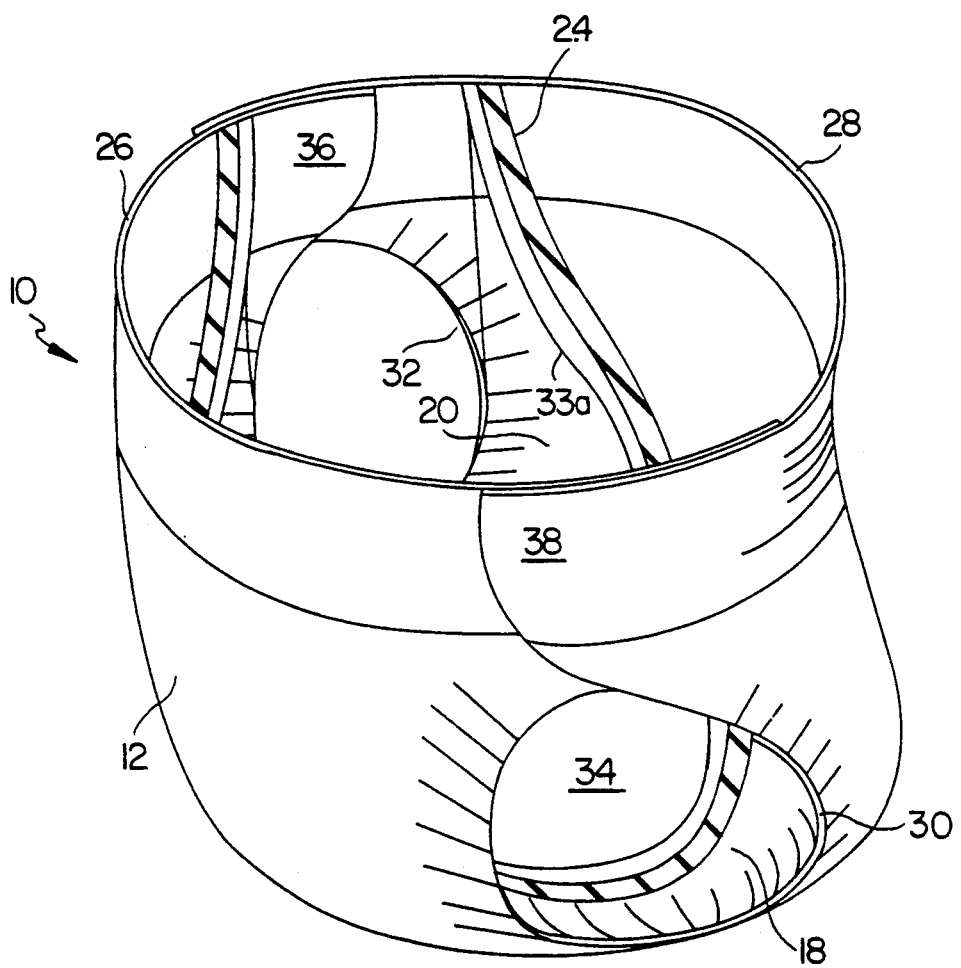
FIG. 6 illustrates a disposable garment according to FIG. 1 as it would be applied to a wearer of the garment.

FIG. 3 shows the garment 10 as if fitted on a wearer. The side margins 30 and 32 are gathered and elasticized to create a better fitting garment which is more capable of retaining bodily wastes. There are a variety of methods for providing elasticized leg openings, and one such method is illustrated in U.S. Pat. No. 4,726,807, incorporated by reference above. Referring again to FIG. 1, to form these elasticized leg openings, longitudinal ribbons 46 of a heat shrinkable polymeric material may be placed along each of the opposed side margins 30, 32 during manufacture, and held in place by the fine hot melt adhesive lines such as 48. FIG. 1 illustrates the garment before heat has been applied to the ribbons 46, which will cause it to form the shirred or wrinkled edge with the accompanying transverse folds as shown in FIG. 6. If an elasticized waist portion with waist gathers are also desired, additional heat shrinkable ribbons 46 may be placed in the boundary area 40 adjacent the first and second waist edges 26 and 28. Of course, it is also common to provide elasticized leg openings utilizing strips of an elastomeric material, such as rubber.

Figure 7:
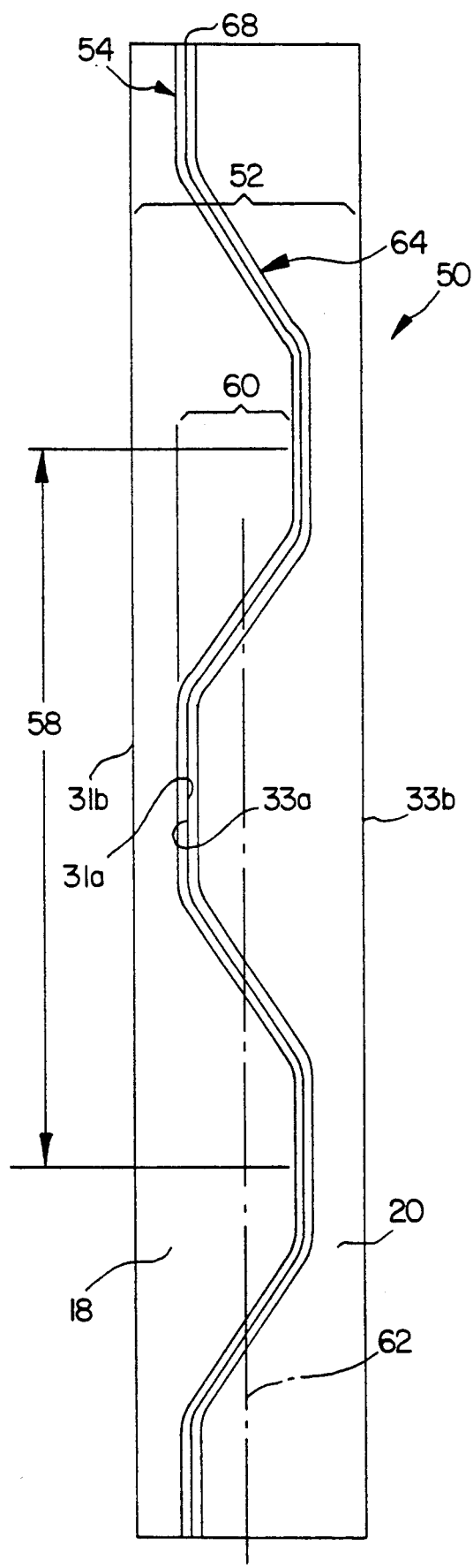
FIG. 7 is a top plan view of the adhesive, elastic member, and a cut pattern of one embodiment of the material used in forming the overlay strips of the present invention.
Figure 8:
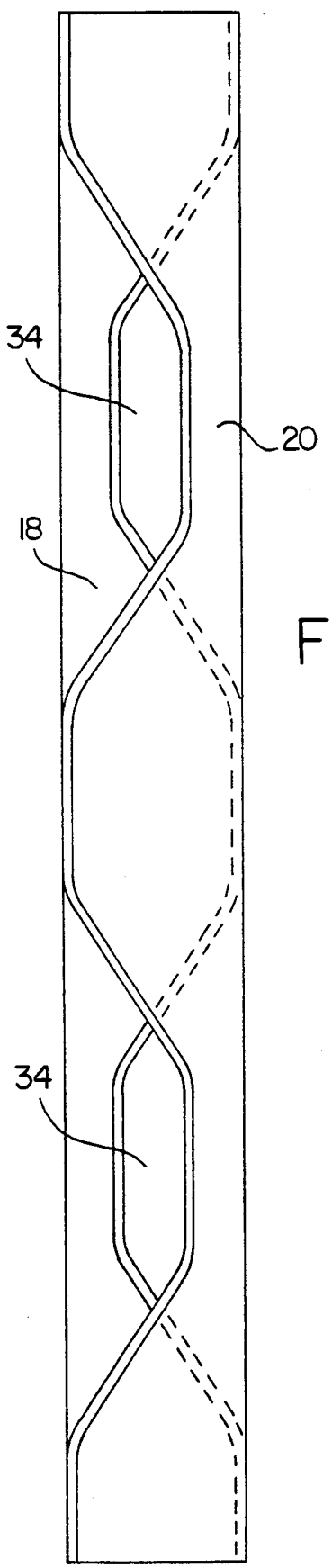
FIG. 8 is a plan view of the overlay strips of FIG. 7 when offset and superimposed.

A method of producing the overlay strips is shown in FIGS. 7-9. In accordance with this method, adhesive is applied in the desired pattern, such as a sinusoidal pattern, to overlay strip forming material 50 of a predetermined width 52. As a specific example, the material 50 may be about the width of the crotch area of the garment, e.g. about six inches. Alternatively, the material may be of a width which is equal to the overall width of the garment, e.g. including the width of waist extensions 36, 38. In this latter case, the second edges 31b, 33b of the overlay strips 18, 20 are severed in the shape of the garment when the garment is made, in which case the extensions 36, 38 are overlayed with the overlay materia, which again may be hydrophobic. In the preferred embodiment, the adhesive is applied in a band 54. The pattern has a pitch 58 is substantially equal to the garment length, defined as the distance between the front waist edge 26 and the back waist edge 28 shown in FIG. 1, and an amplitude 60 which is preferably substantially one half the width 52 of the material 50. In a preferred embodiment, the pattern is substantially symmetrical along a longitudinal centerline 62 of the hydrophobic material 50. Although the method is illustrated with reference to a preferred embodiment which makes use of a sinusoidal pattern, one skilled in the art to which the invention pertains will recognize that patterns varying substantially from a true sinusoid can also be used.

Figure 2:
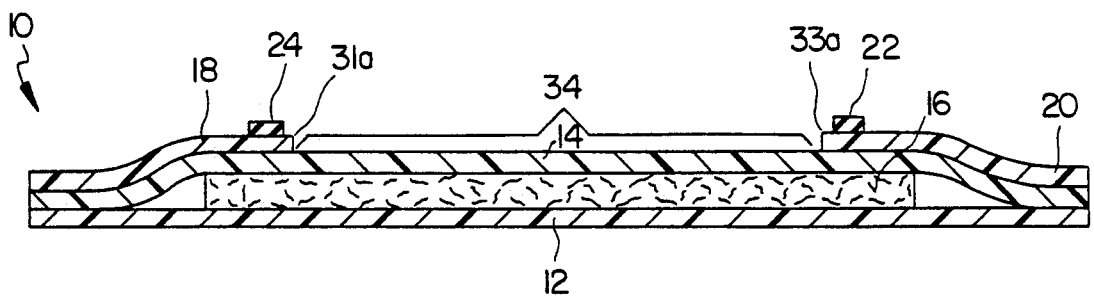
FIG. 2 is a vertical sectional view taken along line 2—2 of FIG. 1 showing just the portion of the garment at the place where the vertical section is taken.

Next, a strip of stretchable material 64, while in a stretched condition, is applied to the adhesive 54 band, following the sinusoidal path of the adhesive. The material 50 is then severed along a common centerline 68 of the pattern, thereby forming the overlay strips 18, 20. The severed edges 31a, 33a thus comprise the inner edge of the overlay strips. Alternatively, separate bands of adhesive may be positioned along or spaced slightly away from the eventual centerline 68. A first elastic member is then secured along the first band of adhesive while a second elastic member is fastened along the second band of adhesive. The material is then severed along line 68, typically leaving the elastic members spaced slightly from the edge of the line of severing (see FIGS. 1 and 2). Also, as previously explained, the edge of the material along the line of severing may be looped over the elastic member and secured, as explained above in connection with FIG. 3.

In these cases, a heat activated stretchable material such as heat activated elastomeric can be used for the elastic material to avoid having to apply stretchable material in a stretched condition. The heat activated stretchable material is simply applied to the adhesive in its original state, then rendered stretchable after adhesion by heating the material to the required temperature.

The above steps for forming the overlay strips 18, 20 shown in FIG. 7 may be performed by an apparatus 80 such as that shown in FIG. 9. The apparatus 80 includes a pair of stationary rollers 82, a pair of oscillating rollers 84 and an oscillating spray head 86. The nonwoven material 50 travels in a leftward direction as indicated in the drawing, between the stationary rollers 82. The oscillating rollers and oscillating spray head are mounted on suitable structure to oscillate back and forth in a direction perpendicular to the direction of travel of the nonwoven material. The oscillating rollers and oscillating spray head may oscillate together or independently. Suitable structures for providing the oscillating motion such as cam shafts, cam gears, or electronically controlled stepping motors are well known in the art. The X-Y control systems commonly used for supporting water knife cutters can also be used with the water knife being replaced by the respective spray head 86 and rollers 84.

The oscillating sprayer 86 operates to apply the adhesive to the nonwoven material along the sinusoidal pattern as described above. The strips of stretchable material 64, 66 are fed through the oscillating rollers 84 and onto the adhesive on the nonwoven material 50. The stationary rollers 82 press the strips of stretchable material onto the nonwoven material. Friction forces in the oscillating rollers 84 can be used to tension the strips of stretchable material to place them in stretched condition when applied to the nonwoven material.

Severing of the nonwoven material into two overlay strips 18, 20 can be performed with a water knife or using any other suitable means.

With reference to FIG. 8, after completion of the above steps, the overlay strips 18, 20 are longitudinally offset by one half the pitch. The overlay strips are then superimposed to form a series of openings 34 between the overlay strips 18, 20.

The superimposed, offset pair of overlay strips 18, 20 are positioned on the exposed inner layer surface 14 of garment 10 as shown in FIG. 1. Typically, these strips 18, 20 in roll stock form are fed on a continuous basis to a garment (e.g. diaper) manufacturing line with the strips being severed transversely simultaneously with the severing of the garments on the line. One of the openings is positioned over a central portion of each garment spaced from the front and back waist edges 26, 28 and the side margins 30, 32 to form the target region 34. The overlay strips 18, 20 are severed along the front edge 26 and back end edge 28 and bonded on all sides of the outer periphery of the overlay strips 18, 20 to the inner layer 14.

Having illustrated and described the principles of my invention with respect to several preferred embodiments, it should be apparent to those skilled in the art that my invention may be modified in arrangement and detail without departing from such principles. I claim all such modifications falling within the scope and spirit of the following claims.

I claim:

1. A method of producing overlay strips for absorbent garments, the method comprising:
   providing a sheet of nonwoven material having first and second side edges and of a length which is equal to the length of multiple garments;
   positioning stretchable material in a repetitive pattern on the sheet, said pattern having a pitch substantially equal to the length of the garment, said pattern alternately approaching the first side edge of the sheet and then the second side edge of the sheet; and
   severing the sheet along said pattern to form two continuous strips with stretchable material extending substantially continuously along the longitudinal severed edge of each strip, each strip having alternating wide and narrow portions.

2. A method according to claim 1 in which the pattern is symmetric about the longitudinal centerline of the sheet.

3. The method of claim 1 wherein the step of positioning stretchable material in a repetitive pattern on the sheet comprises:
   applying adhesive to the top of the sheet along a repetitive pattern; and
   applying a narrow strip of stretchable material, while in a stretched condition, to said adhesive along said adhesive pattern; and
   the severing step comprising the severing of the sheet and narrow strip of stretchable material.

4. The method of claim 1 wherein the step of positioning stretchable material in a repetitive pattern on the sheet comprises:
   applying adhesive to the top of the sheet along a repetitive pattern;
   applying a first narrow strip of stretchable material, while in a stretched condition, to the adhesive; and
   applying a second narrow strip of stretchable material, spaced from the first strip, while in a stretched condition, to the adhesive; and
   the severing step comprises the step of severing the sheet between the first and second strips of stretchable material.

5. The method of claim 1 wherein the stretchable material is a heat activated stretchable material and the method includes the step of heating the stretchable material to render the material stretchable.

6. A method of producing an absorbent garment comprising:
   (a) providing a garment body having front and back waist end edges, a moisture-impervious backing layer, a nonwoven moisture-pervious inner layer having an inner waste-receiving surface, and an absorbent core layer between said inner and backing layers;
   (b) providing an overlay sheet of nonwoven material having first and second side edges and of a length which is equal to the length of multiple garments;
   (c) positioning stretchable material in a repetitive pattern on the overlay sheet, said pattern having a pitch substantially equal to the length of the garment body, said pattern alternately approaching the first side edge of the sheet and then the second side edge of the sheet; and
   (d) severing the overlay sheet along said pattern to form two continuous strips with stretchable material extending substantially continuously along the longitudinal severed edge of each of said continuous strips, each strip having alternating wide and narrow portions;
   (e) longitudinally offsetting one of said continuous strips by substantially one half the pitch of said pattern;
   (f) superimposing said continuous strips, thereby providing a series of openings between said continuous strips;
   (g) positioning said continuous strips on the inner waste receiving surface of the garment body to place one of said series of openings over a central portion of the garment body;
   (h) attaching said continuous strips to the garment body; and
   (i) severing said strips along the front and back waist end edges of the garment body as the garments are severed.

7. A method according to claim 6 in which the pattern is symmetric about the longitudinal centerline of the sheet.

8. The method of claim 6 wherein the step of positioning stretchable material in a repetitive pattern on the sheet comprises:
   applying adhesive to the top of the sheet along a repetitive pattern; and
   applying a strip of stretchable material while in a stretched condition, to said adhesive along said adhesive pattern; and the severing step comprising the severing of the sheet and strip of stretchable material.

9. The method of claim 6, wherein the step of positioning stretchable material in a repetitive pattern on the sheet comprises:
applying adhesive to the top of the sheet along a repetitive pattern;
applying a first narrow strip of stretchable material, while in a stretched condition, to the adhesive;
applying a second narrow strip of stretchable material, spaced from the first strip, while in a stretched condition, to the adhesive; and
the severing step comprising the step of severing the sheet between the first and second strips of stretchable material.

10. The method of claim 6, wherein the stretchable material is a heat activated stretchable material and the method includes the step of heating the stretchable material to render the material stretchable.

11. The method of claim 5, wherein the step of positioning the stretchable material comprises applying adhesive to the top of the sheet along a repetitive pattern, and applying a narrow strip of stretchable material to said adhesive along said adhesive pattern.

* * * * *